United States Patent [19]

Cuervo

[11] Patent Number: 4,785,797
[45] Date of Patent: * Nov. 22, 1988

[54] METHOD AND APPARATUS FOR THERAPEUTIC MOTION AND SOUND TREATMENT OF INFANTS

[76] Inventor: Armando A. Cuervo, 710 E. Walnut St., Westerville, Ohio 43081

[*] Notice: The portion of the term of this patent subsequent to Jul. 21, 2004 has been disclaimed.

[21] Appl. No.: 72,969

[22] Filed: Jul. 14, 1987

Related U.S. Application Data

[63] Continuation-in-part of Ser. No. 553,317, Nov. 18, 1983, abandoned, and a continuation-in-part of Ser. No. 712,561, Mar. 15, 1985, abandoned, and a continuation-in-part of Ser. No. 848,454, Apr. 4, 1986, Pat. No. 4,681,096.

[51] Int. Cl.4 .............................................. A61H 1/00
[52] U.S. Cl. ........................................ 128/33; 600/28
[58] Field of Search .................... 128/33, 34, 1 C, 36; 5/109

[56] References Cited

U.S. PATENT DOCUMENTS 4,681,096 7/1987 Cuervo .................................. 128/33

Primary Examiner—Richard J. Apley
Assistant Examiner—J. Welsh
Attorney, Agent, or Firm—Robert B. Watkins

[57] ABSTRACT

A method and apparatus for soothing and pacifying crying and colicky infants including apparatus and methods to impart a rhythmic cyclic motion of displacement to the surface on which the infant is supported, at a frequency between about ten and forty-three cycles per second with an amplitude of displacement between about one-eighth and one-hundredth of an inch. In a preferred embodiment, methods and apparatus are included for imparting sound at an intensity of between about sixty and eighty decibels at a frequency range of substantially between about two hundred and four thousand Hertz.

9 Claims, 4 Drawing Sheets

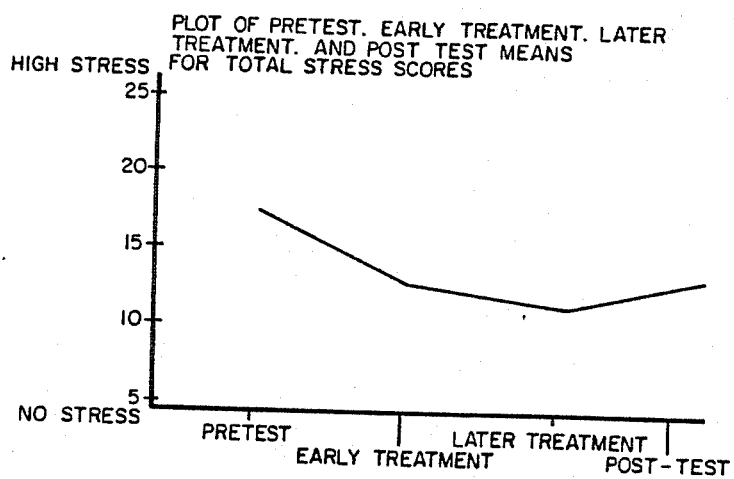

METHOD AND APPARATUS FOR THERAPEUTIC MOTION AND SOUND TREATMENT OF INFANTS

This patent application is a continuation-in-part of U.S. patent application Ser. No. 553,317 filed Nov. 18, 1983 now abandoned, and a continuation-in-part of U.S. patent application Ser. No. 712,561 filed Mar. 15, 1985 now abandoned, and a continuation-in-part of U.S. patent application Ser. No. 848,454 now U.S. Pat. No. 4,681,096 filed 4/4/86, all by the same inventor as this application.

TECHNICAL FIELD OF THE INVENTION

This invention relates to a method and apparatus for soothing and pacifying crying and colicky infants. More particularly, it is in the field of methods and apparatus for imparting rhythmic cyclic motions and/or sounds which have a therapeutic effect on the environment of an infant.

BACKGROUND ART

The problem of soothing and pacifying restless, distressed, crying, and often termed colicky infants, has been with the human race since early times. It has long been practiced to impart vibrational rhythmic repetitory motion to the infant in an effort to sooth and pacify. Success is often dependent on unknown factors, has not been predictable, and may be exasperatingly unobtainable in particular circumstances.

This has been a source of frustration to the parents, and those others in attendance, as well as the pain distress to the infants.

These problems have attracted the attention of previous inventors and many authors. A typical example of a prior art patent in U.S. Pat. No. 3,311,935—Petty, which discloses a vibration imparting device for attachment beneath a crib/bed for infants. A frequency of about three hundred and fifty RPM (5.83 cylces per second) is stated to be satisfactory.

U.S. Pat. No. 2,932,821—Horton, discloses an infant pacifying device which emits a audible buzzing sound accompanied by a mild vibratory effect such as are encountered by the operation of an electric shaver or the like.

U.S. Pat. No. 3,799,154—Knop, reveals a device for insertion under the mattress of a bed that imparts vibration thereto. The patent is directed primarily to adult massage. An eccentric weight is rotated to provide cyclic oscillation or displacement.

U.S. Pat. No. 3,872,526—Betts, shows a vibratory waterbed providing specified non critical frequencies of between ten and eighteen hundred cycles per second. Because of the fluid nature of a waterbed, amplitude would vary from place to place and would be uncontrollable.

U.S. Pat. No. 3,503,389—McKee et al., discloses a vibration inducing apparatus for placement between the frame and boxsprings of a bed with a teaching that the vibrations are between three hundred and fifty and one thousand RPM, (which is equivalent to between 5.8 and 16.7 cycles per second).

U.S. Pat. No. 3,035,572—Houghtaling, discloses a vibrator attached beneath the springs of a bed, couch, or cushion. The Patentee shows no specific teaching concerning vibratory frequency or amplitude and any connection thereto with therapeutic results.

U.S. Pat. No. 3,019,785—Eiden, reveals a vibratory massage cushion having eccentrically weighted rotating motors to produce an oscillating effect to an elongated member that is intended to slide between a matress and bedspring or other support means. There is no teaching of critical amplitude and the emphasis is on massage. Sound is not a teaching in this patent.

An article published in The Journal of Psychology, 1971, 78, 269–276 by Leland D. Van Den Daele entitled "Infant Reactivity to Redundant Proprioceptive and Auditory Stimulation: A Twin Study"—discusses the activity of infants under the influence of motion and sound. The activity was conducted with a "displacement of three inches at either thirty or sixty cycles per*minute*" (emphasis added) and an eighty decibel (DB sound) thirty inches away from the subjects. The displacement disclosed is a "rockerbox", being intended to imitate the normal maternal head to toe rocking action.

U.S. Pat. No. 2,512,621—Emerson, discloses a vibrator panel comprising a thin stiffly resilient panel which is operated at an amplitude ("eccentricity") of the order of five sixteenths of an inch.

Even though there have been patented approaches to the problems and fussiness in young infants, the sympton of colic remains one of the most common encountered in pediatric practice today. Much has been written in the literature on this subject including the references listed further in this specification.

Although colic is difficult to define, it is perceived as an unexplained paroxysms of irritability, fussing, crying and often sustained screaming accompanied by indication of colinic peristalsis. The symptoms usually start after feeding, and they may occur in regular twenty-four hour cycles that are quite predictable. Symptoms are reported to be worst late in the day.

The pediatric text authored by Kempe, Silver, and O'Bryen (1978), presents a typical description:

"Colic or paroxysmal fussing is a common problem in young infants. It is most common in the evening. It may build up in crescendo, with the baby drawing his legs up onto his abdomen, and is frequently relieved by the passage of flatus. This period usually begins at age 2–3 weeks and disappears by 10–12 weeks—so called '3-month colic'. The course is not clear, but 'developmental colic' may be related to overready response to stimulation, irregular gastrointestinal peristalsis, and other as yet unintegrated autonomic functions characteristic of the first 2–2 months." (p. 55).

the incidents in the general population of newborn to three month old infants is reported at nine to twenty-three percent. In low birthweight infants colic occurs at 11.4 percent of the population. With 3.6 million babies born in the United States each year this represents a significant number of affected infants.

It has been known as a treatment that rhythmic rocking motion or rocking vibration has a soothing effect on fussiness and distress in infants. Recommendations on easing colicky episodes in infants by rocking or rhythmic motion are found in pediatric texts. However, such recommendations have been generalized.

It is an object of this invention to provide specific ranges of motion frequency and amplitudes, as well as sound for the soothing and pacification of infants who are diagnosed as having colic and as a corollary, to provide comfort to infants during spells of fussiness and crying in general.

The advantages from the treatment of colic by vibratory motions and/or sound are clear. Mild well-timed periods of stimulation have no known ill effects, and when effective in easing the infant's distress, may decrease the need of drugs such as phenobarbital, bentyl, etc. In addition to the concen about harmful effects of drugs, there is serious doubt that conventional drug therapy is effective. The possibility of drug tampering is circumvented by the non invasive treatment with this medical device. In addition to easing the infant's pain and discomfort, providing rhythmic motion and sound to soothe the infants eases the strain on parents, decreasing the amount of child abuse associated with colic and increasing the likelihood of improving the quality of the mother-infant relationship. As well, there are reports of parents using potentially dangerous home remedies in their attempt to comfort the distressed infant. With a product and process that provides safe treatment for the symptoms of colic available to parents, there may be fewer ill advised attempts to ease the infants discomfort.

Demographic studies show 3.73 million babies born in the USA in 1982 projecting up to 3.99 million by 1986 and tapering down to 3.55 million by the year 1992.

Taking into consideration the incidence of colic ranging from nine to twenty-three percent, the affected population today ranges from three hundred thirty-six thousand to eight hundred fifty-seven thousand colicky babies. In 1986 it will peak at a range of three hundred sixty thousand to nine hundred seventeen thousand colicky babies. Thus it will be seen that there is a strong need for a medical device and process which will ease the discomfort of fussy and colicky infants with significant and predictable degrees of success without the use of drugs with questionable long term effects.

Predictably effective motion and/or sound simulation thus has the object of (a) easing infant pain and discomfort; (b) decreasing the use of drugs; (c) enhancing the quality of parent/infant relationship; and (d) decreasing the incidence of child abuse associated with paternal frustration or the administration of potentially dangerous home remedies.

DISCLOSURE OF THE INVENTION

In summary, this invention is a method of soothing and pacifying infants including the steps of placing the infant on a supporting substrate or surface in a comfortable position and then imparting a rhythmic cyclic motion displacement means to the supporting surface and creating on the surface a rhythmic cyclic motion at a frequency range which has been found to be particularly effective and beneficial. The frequency range on the surface is between about ten cycles per second and about forty three cycles per second and an amplitude of displacement between about one eighth of an inch and one hundredth of an inch. A further summary of the invention includes apparatus for soothing and pacifying a colicky infant which is supported on means arranged to provide a potentially comfortable position comprising means for imparting a rhythmic cyclic motion of displacement to a supporting means creating at the surface of the supporting means a rhythmic cycling motion of displacement in a range between about ten cycles per second and forty-three cycles per second and the amplitude of displacement being in a range between about one eighth of an inch and about one hundredth of an inch.

In a preferred embodiment of the invention sound is selectively and simultaneously imparted within the hearing range of the infant, and controlled within an intensity range between about sixty decibels to about eighty decibels within a frequency range of substantially between about two hundred Hertz and about four thousand Hertz.

The specific frequency and displacement of the supporting means and the infant may be adjustable within the range, and maybe established at an optimum for a particular infant.

It is an object of the invention to operate the method and apparatus in a specific region of rhythmic cyclic motion that has been found to be surprisingly critical and significantly more effective than prior art in the soothing and pacification of infants, and particularly infants having colic.

A further object is to impart sound within the hearing of the child to further enhance the operation of the method to achieve optimum results and therapeutic effect.

The foregoing and other advantages of the invention will become apparent from the following disclosure in which a preferred embodiment of the invention is described in detail and illustrated in the accompanying drawings. It is contemplated that variations in structural features and arrangement of parts may appear to the person skilled in the art, without departing from the scope or sacrificing any of the advantages of the invention.

BRIEF DESCRIPTION OF THE DRAWINGS

FIG. 9 is a graph showing Pretest, Early Treatment, Later Treatment, and Post Test mean test results of parental stress during the treatment of colicky infants.

BEST MODE FOR CARRYING OUT THE INVENTION

Figure 1:
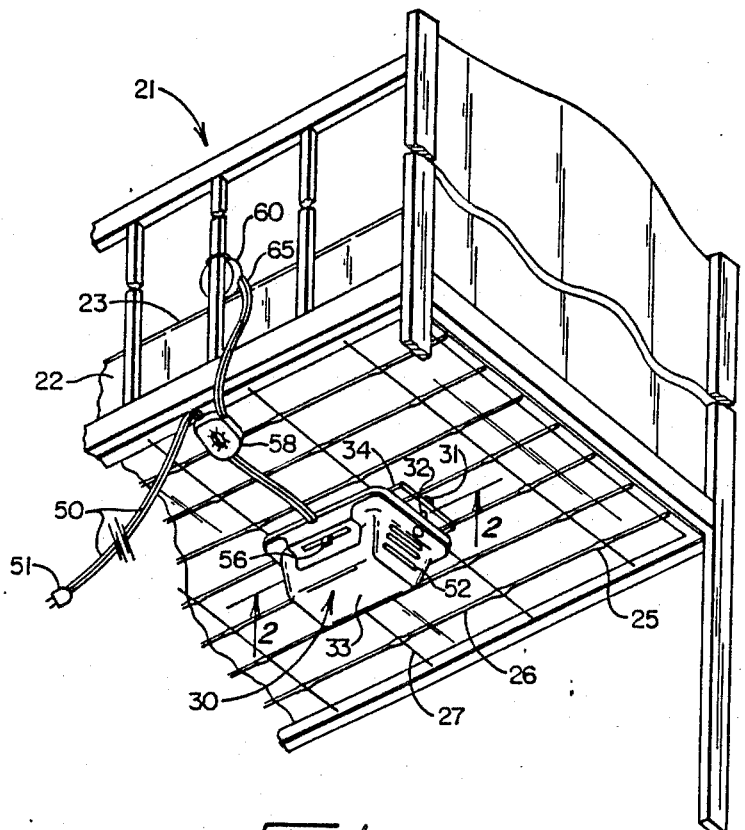
FIG. 1 is a perspective view of an arrangement in which the method of this invention may be practiced with a preferred embodiment of the apparatus of this invention.

Referring to FIG. 1, an infant crib/bed 21 includes a support means or mattress 22 having a surface/substrate 23 on which an infant may be placed in a potentially comfortable position. The mattress 22 is supported on springs 25, typically having longitudinal members 26 and lateral members 27. Other spring constructions (not shown) conventionally include flexible membranes and coil springs arranged on a frame.

A power means 30, typically shown as an electric motor is substantially fixedly attached to the springs 25 by bolts 31 passing through holes 32 in a housing 33 which supports the power means 30. The bolts 31 also pass through a clamping means 34, which is typically shown as a plate spanning the elements 27 and 26 of the springs 25.

Figure 2:
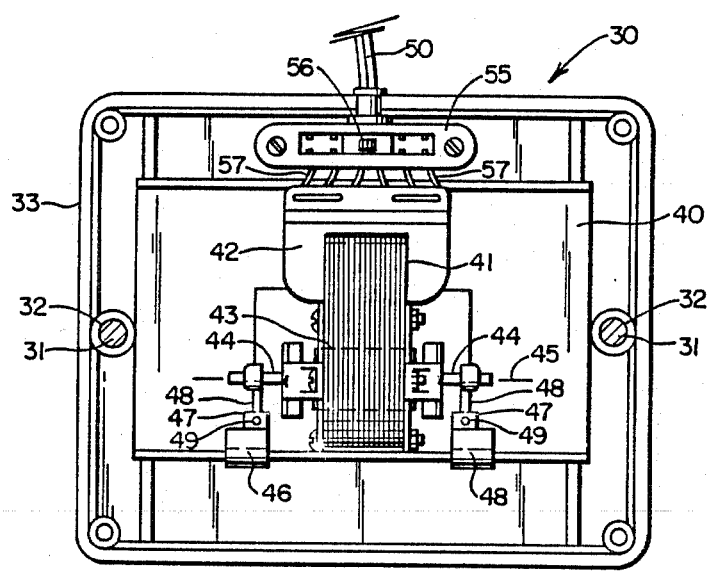
FIG. 2 is an sectional plan view of the apparatus of the invention taken along the line 2—2 of FIG. 1.

Referring also to FIG. 2, power means 30, when typically an electric motor, includes a base 40, connected to the housing 33, which support and encompass a stationary core means 41 having a coil 42. A rotatable core 43 is supported on a shaft 44 which turns on an axis of rotation 45.

The shaft 44 carries at least one eccentrically positioned weight 46 by means of a fixedly positioned collar 47 having an arm 48. The eccentric weight 46 is positioned on the arm 48 by means of a threadedly engaged set screw 49 in a conventional fashion. In FIG. 2, two oppositely positioned eccentric weights are shown, for balancing purposes, since only one may be necessary.

In well known electrical circuitry, the coil 42 is connected at intermediately positioned points to provide a series of contacts to a source of electric power, such as through a covered wire cord 50, a plug 51, and a convenience outlet (not shown).

In the interest of reliability and safety the housing 33 is provided with vents 52 for the passage of environmental cooling air, which may be propelled by a fan (not shown) on the shaft 44. A multiple positioned switch 55 having a knob/button 56 is operable to connect the power to intermediate points on the length of the coil 42 through connecting wires 57. By placing the knob/button 56 at various positions, the power may be cut off or directed to various segments of the coil providing adjustments in the power to the motor 33 which in turn will provide adjustments to the speed of the motor operation. Alternatively, analog speed adjustment devices may be used.

A mechanical or other type of timer 58 may be provided in the power supply cord 50 or battery providing the capability of determining and adjusting the amount of time that power is supplied to the power means 30, so that they can be conveniently operated for a specified and predetermined period of time.

The base 40 and the housing 33, as well as various other components of the apparatus, may be constructed of metal of plastic and stamped or molded as the situation requires.

In the operation of the method and apparatus of the invention the power means 30 is substantially fixedly attached to the support means on which a fussy, colicky infant is placed. The knob 56 is operated to turn the apparatus on, and the timer may be set for a convenient period of time which may usually be in a range of up to about one-half hour.

With the infant in a potentially comfortable position on the surface 23, the mattress 22 imparts rhythmic cyclic motion of displacement to the mattress and surface, and vicariously to the infant thereon.

Since my earlier U.S. patent application Ser. No. 848,454 was filed of which this is a continuation-in-part, further measurements have been made as to the frequency of vibration "seen" (felt) by the infant. In the earlier tests the means for imparting motion such as the motor 30 and weights 46 apparatus was tested and rated by the manufacturer according to the numerical frequency ratings discussed in that application. Such rated power units were tested by the manufacturer when the apparatus 30 was attached to a manufacturing bench in the assembly process. Since that time, further tests have revealed that when motor 30, rated at between 2500-2700 RPM at the assembly bench, were attached to a crib and they imparted motion thereto, the mass and resonance of the crib system produced a vibration on the surface of a crib of about 2600 RPM (43 cylces per second). On the other hand, surprisingly it has now been determined, that power unit motors 30 rated at the assembly bench, at 1500 to 1650 RPM only produce a frequency of vibration of about 700 RPM (10 or 11 cycles per seond) on the surface of the crib. Therefore, there is a phenomenon involving the calibration relationship of the effective ranges between the manufacturing assembly bench and the actual crib or support surface.

Such measurements are not a change in the understanding of or effect observed in the tests, but are a redefinition of lower frequency ranges where beneficial effects also take place. Such improved and refined measurements and definition serve to further clarify the scope of the invention and represents the more precise description of the methods and best modes for carrying out the invention; since it does not appear that the prior art perceived the distinction and the lack of correlation (calibration phenomena) between assembly bench and crib frequencies at the lower frequencies. This phenomena of the non-linear function of correlation at the lower speed is probably a first observation of the lack of linear correlation in the further testing of these types of apparatus, since it is not mentioned nor discussed in the prior art, and the prior art practitioners were not aware of the important distinctions involved.

Voltage changes at the input of the power means has only slight effect on the rate of vibration on the crib surface, for instance a difference between 103 and 118 volts has made only a difference of 1.4 cycles per second.

Variation in the weight of the baby and the weight of the mattress were inconsequential.

The difference between new and used crib springs only produced a difference of less than 1 cycle per second.

The speed increased only about 1 cycle per second at the lower end of the speed range scale and about 6 cycles per second at the higher speed range scale after an apparatus had warmed up by operation for five minutes.

In view of this newly discovered information obtained herein, it is believed that the applicant's invention has a broader scope of benefits as presented herein and as defined in the appended claims.

It has been found that in the operation of the method that a motion of displacement at the surface of the substrate or support at a frequency of between about ten cycles per second and about forty-three cycles per second with the amplitude of displacement between one eighth of an inch and about one hundredth of an inch produces surprisingly predictable reduction in the fussiness and colicky stress among a group of infants to whom the method has been applied.

The term displacement, as used herein, means the distance from one maximum position in one direction to another second maximum position in the opposite direction. When the power means is a rotational motor with eccentric weights on the shaft, one revolution of the shaft produces one cycle of motion including a maximum displacement in one direction and return to maximum in the opposite direction.

When the motor is in operation, the shaft 44 rotates swinging the weights 42 on the arms 48 in an arch about the axis of rotation 45 creating a rhythmic cyclic motion of displacement through the power unit 30, the springs 25, the mattress 22, and the substrate surface 23 where the infant is lying. This motion is imparted to the infant. The amount of displacement of the surface and its cyclic frequency is determined by size of the eccentric weights 42 and their positions on the arms 48 as fixed by the set screws 49. By the appropriate combination of power imputed and positioned weights, the displacement and frequency at the surface is adjusted within the ranges found to be especially beneficial and predictably effective as therapeutic treatment of the condition of colic.

In a test group of infants it has been found that discomfort, fussiness, and colicky distress can be predictably relieved or lowered in a significantly large percent (90%) of the test situations when rhythmic cyclic motion of displacement is imparted to the substrate and creates a frequency at the surface between about ten cycles per second and about forty-three cycles per second with the amplitude of displacement between one eighth of an inch and about one hundredth of an inch.

On the other hand, with other frequency or displacements outside of the range of practice of this invention, such predictably favorable therapeutic effects can not be obtained. As experience has shown in the prior art practices, many frustrating unsuccessful circumstances will result.

Figure 3:
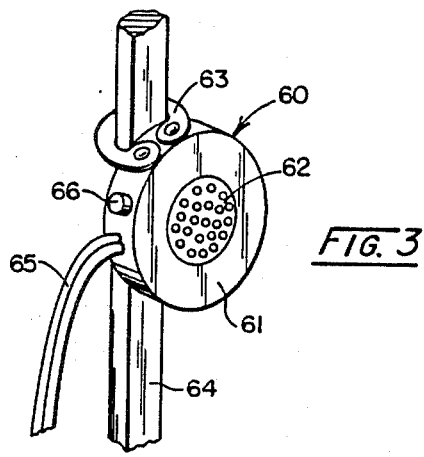
FIG. 3 is a perspective view of a portion of the apparatus of this including a sound generator portion of the apparatus of this invention.

Referring to FIG. 3, and again to FIG. 1, a sound generator 60 in a housing 61 having a speaker 62 is constructed with straps 63. The straps 63 are constructed to encircle a rung 64 of the crib/bed 21, holding the generator 60 in a position to impart sound within the hearing range of an infant supported on the surface 23. The sound generator mechanism within the housing 61, may be a semiconductor microchip or other transistor type device capable of producing an audible sound in the intensity range of between sixty and eighty decibels and a frequency range of substantially between about two hundred and about four thousand Hertz. Such sound is generally analogous in character to that of wind motion sounds outside the windows of a moving automobile traveling on the highway at 45-55 miles per hour. Power is provided to the generator 60 through an electric wire 65 that is connected to the switchbox 58; and on through the wire 50 and connector 51. Alternatively, power may also be supplied by battery means.

A combination on/off and volume control switch 66 is connected to the generator 60 with other conventionally constructed circuits within the generator to provide sound from the speaker 62 when selectively chosen by the user.

In the continuing progress of miniaturization of electronic components and within the state of present technology it is believed that the generator 60 may be constructed in a much smaller size than that described above and may be only the size of a small coin or hearing aid by way of comparative size and technology.

The generator 60 is constructed to generate a random noise and is provided with a low pass filter to provide the appropriate spectrum of frequency and intensity. In a module constructed for test purposes a random noise signal was low pass filtered (cut off at eight hundred Hertz) with a filter having a reject band attenuation of approximately 24 dB/octave.

The overall level of the signal was adjusted to be about seventy five dBA. It was found that the maximum level (seventy four db) was recorded in the span centered at five hundred Hz; slightly lower levels were recorded in the two hundred fifty Hz and one thousand Hz bands. Subjectively, the sound was noted to be moderately loud but not objectionable. There is no evidence to suggest that exposure to this noise for even up to eight hours would in any way damage hearing. It is well below the eighty five dBA level stipulated for an eight hour exposure by Occupational Safety and Health Administration Rules. Moreover, it is primarily low to medium frequency which in terms of this effect on hearing, is even less problematic than higher frequency noises.

The method and apparatus of this invention has been evaluated and tested in controlled studies research grants by the National Institute of Health (NIH), having a Federal Identification Number 31-102673. Research was conducted in two phases.

The $500,000 research grant controlled study was performed over the 4 year grant period resulting in being cleared for national marketing as a medical device with a medical claim on soothing colic.

While the Phase I Program was primarily intended to identify techniques for further evaluation in a larger group of subjects, the results of the Phase I clinical trails produced significant confirmation that there is an identifiable critical range of frequencies and amplitudes which produced surprising results.

Phase I results have shown that statistically significant therapeutic improvement can be obtained in the soothing and pacification of colicky and crying infants when the method and apparatus are to produce at the support surface the range of about ten cycles per second and about forty-three cycles per second. These results were obtained by testing eleven infants under controlled conditions in clinical trails, in which the infants were subjected to three ranges of frequency and amplitudes provided by apparatus and methods similar to the invention.

As an example, a first test procedure was to identify the degree of fussiness and crying of a colicky infant over a first period of time as a baseline. Then as a second test, the infant was placed in apparatus similar to this invention. The infant was subjected to vibrations of minimal amplitude and the no load speed of the electric motor. This was a placebo condition.

The infant was then tested in a range below about 10 cycles per second and no relief was perceived in 9 out of 11 subjects.

After a period of testing in this range, the infant was subjected to a second range with the frequency varible within the range of 10 to 32 hundredth of an inch to about an eighth of an inch. The degree of fussiness and crying of the colicky infant was recorded by trained observers and mothers.

Finally, the infant was subjected to a third method for a controlled period of time, in a range of about 33 to 50 cycles per second at an amplitude between one hundredth and one eighth of an inch. Those subjected to a range exceeding 43 cycles per second became irritated and alerted.

The results were statistically determined among the group of infants tested in Phase I to be significant at a probability level less than 0.025. Results were determined by controlled questionnaire responses of trained observers and mothers whose babies were in the tests.

The number of trained observers and mothers reporting improvements in the babies (i.e. the colic lessened) is significant at a probability level less than 0.025. This was determined by conducting a sign-test with a P equals 0.5 value. The data was collected by trained observers and mothers were interviewed following their use of the apparatus in the range of 33 to 43 cycles per second. Of the eleven subjects in the study, ten improved. This ratio of nine or eleven ration was highly significant (e.g. at the 0.025 level).

From the foregoing, it was to be expected that Phase II results would further amplify and verify the previous confirmation that there is an unexpectedly surprisingly successful method of operating the motion apparatus of this invention. The expectation proved correct. It was also found that the synergistic effect of sound produced optimum effectiveness at the lower ranges of 10-32 cycles per second with an optimum of 15. Vibration alone was more effective at the higher end of the range of 32-43 cycles per second.

Phase II Research

Accordingly, Phase II research was conducted in an Experiment One.

The purpose of Experiment One (50 subjects) was to determine the effectiveness of rhythmic motion on reducing/relieving symptoms of infant colic. Based on the results of the Phase I pilot study, two levels of rhythmic motion were tested in Phase Experiment One. In addition, auditory simulation was systematically introduced to determine whether or not sound also facilitates the treatment. A 2×2 factorial design was used to analyze the time-sample behavioral measures of infant response.

Colic Severity Rating Scale

Observations of the severity of colic behavior were conducted using the direct interval recording method. Eighty-four observations were taken on each subject over the course of 21 minutes. The first three minutes were a pre-treatment (baseline) period, followed by a 15 minute treatment and then a three minute post-treatment period. Scores on each observation for each 15 second interval were summed. This sum was then used to calculate the mean for the pre-treatment, treatment, and post-treatment phases. A score of 6 equaled intense colic and 0 equaled no colic.

The colic severity score for each 15 second interval was derived in the following way:
1. The infants' sound level was observed and rated;
   If no sounds were made the behavior was scored 0.
   If the sounds were fuss the behavior was scored 1.
   If the sounds were cry the behavior was scored 2.
   If the sounds were wails the behavior was scored 3.
2. The infants' colic movements were observed and scoted as present or absent(behavioral definition available);
   a. Arms/hands 1/0
   b. Arching of back 1/0
   c. legs/drawn up 1/0
3. The sound rating score was then added to any presence of these colic movement scores so that in any given 15 second interval the colic severity score could range between 0 and 6.

Interrater agreement was established in a range between 92% and 99%, with a median of 97%, between each pair of trainees and trainer.

Experimental Design

The reseach design for Phase II Experiment One was a 2×2 factorial design with repeated measures where the independent variable consisted of two levels of motion rate and two levels of auditory stimulation.

It was found in the operation of the apparatus devices that the speed increased slightly as the apparatus warmed up. Consequently the motion varied somewhat to a minor degree.

Twelve subjects were treated with high motion rate without sound and fourteen additional subjects were treated with high motion rate with sound adjusted between about eighty and sixty decibels intensity and composed frequencies between about eight hundred and four thousand Hertz.

In a similar manner, twelve subjects were treated with low motion rate without sound and twelve subjects were treated with low motion rate with sound adjusted as previously described above. The exact frequency of vibration, amplitude, sound frequency, and sound intensity varied slightly due to instrumentation limitations. These factors varied within the ranges set and averaged during optimum results to be about: low motion rate equals about fifteen cycles per second, high motion rate equals about thirty eight cycles per second, sound intensity equals about seventy five decibels, and sound frequency equals about nine hundred fifty Hertz.

As a result of the various treatments, it is believed the average results stated above should be the optimum target ranges for the practice of the invention that are most likely to provide the best therapeutic benefit for the largest number of infant subjects.

The averaged optimum motion rate is believed to be about fifteen cycles per second.

The repeated measures occurred in two ways. First, each subject was observed on four separate occasions over a two week period. Each observation was designed such that the infant was experiencing a colic episode when the observation began. Second, within each observation period, a total of eighty-four (fifteen second duration) behavioral observations were made according to the process described above.

Procedures

The experimental procedure consisted of three phases—pre-treatment, treatment and post treatment.

During pre-treatment, the colicky infant, displaying observable signs of colic, was placed in the center of the crib. The infant was observed by a trained observer for three minutes according to protocol described above. This baseline period was followed by a fifteen minute treatment period where one level of motion rate and one level of sound was introduced for the entire treatment period.

Each experimental motor was constructed such that only one level of motion rate was possible with any given motor.

For those subjects receiving the sound condition, the seventy five DB sound was re-set by an audiologist using a sound meter when the sound generator was fixed to the infants crib. The sound switch was activated during the treatment phase. Following the baseline and treatment phases, the motion apparatus and sound generator (if sould was used) were deactivated during a three minute post treatment observation phase. Neither parents or the observers were able to alter the frequency and amplitude of the motion or the sound level of the generator.

Colic severity data from each of the children was collected, and analyzed. To simplify presentation, the data for each 15 second interval was averaged across the three minutes of pre-treatment, fifteen minutes of treatment and three minutes of baseline for four separate days of observation. The four-fold table presented below contains the sample size of the grouping, the average pre-treatment score, the average treatment score and the average post baseline score.

|  |  | No Sound Mean |  | Sound Mean |  |
|---|---|---|---|---|---|
| Low Motion | Baseline | 3.3 | Baseline | 3.6 |
|  | Treatment | 1.5 | Treatment | 1.1 |
|  | Post-Tmt | 1.4 | Post Tmt | 1.8 |
|  | N = 12 |  | N = 12 |  |
| High Motion | Baseline | 3.4 | Baseline | 3.5 |
|  | Treatment | 2.2 | Treatment | 1.7 |
|  | Post-Tmt | 1.7 | Post Tmt | 1.9 |
|  | N = 12 |  | N = 14 |  |

The overall statistics show a significant decrease between the pre-treatment (colic) scores and the colic scores during the treatment with imparted motion. The difference between the overall pre-treatment mean (3.54) and the treatment mean (1.65) is 1.89, which is statistically significant at the $p<0.01$ level. Thus, there is an effectiveness for the motion apparatus and method which decreases colic severity. This finding is reinforced by the number of children who show a decrease of some kind between pre-treatment and treatment. Ninety four percent (94%) decreased by at least 0.1 of a colic score. Setting the expected probability at $p=0.5$, the number of children showing a decrease in colic is significant, using a sign test, at the $p<0.01$ level. If one considers only those children who improve by 0.5 of a colic score, the proportion (44/50) 88% is still significant at the $p<0.01$ level.

Considering the question of whether a low or high Motion Rate (MR) is more effective and whether sound supplements increase the motion effectiveness, we see that three* of the four treatments perform virtually the same with significant results.

| Treatment or Group Mean | Average Difference Between Pre-Treatment and Treatment |
|---|---|
| Low MR; No Sound | 1.8* |
| Low MR; Sound | 2.5 |
| High MR; No Sound | 1.2* |
| High MR; Sound | 1.8* |

However, note that the low level (MR) with sound improves colic scores by over 1.4 times the improvement found with the next closest treatment 6(High MR; Sound). thus, it appears that the Low MR with sound treatment is the most effective and should be the best mode in treating colic based on the current data.

In summary, this medical device and method, irrespective of treatment mode, lessened colicky behavior based on differences between means and based on the proportion of infants showing improvement even at a cut-off level of one-half a colic score. Also, it appears that the low MR with sound is more effective than the other three treatment modes, although the others are surprisingly good.

Figure 4:
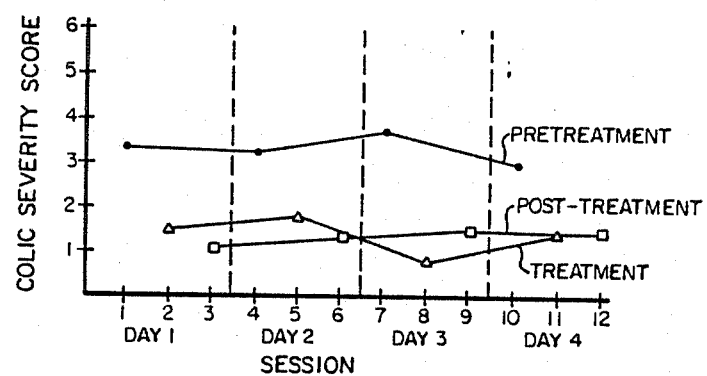
FIG. 4 is a graph showing the data gathered during the low motion rate and no sound of the invention.
Figure 5:
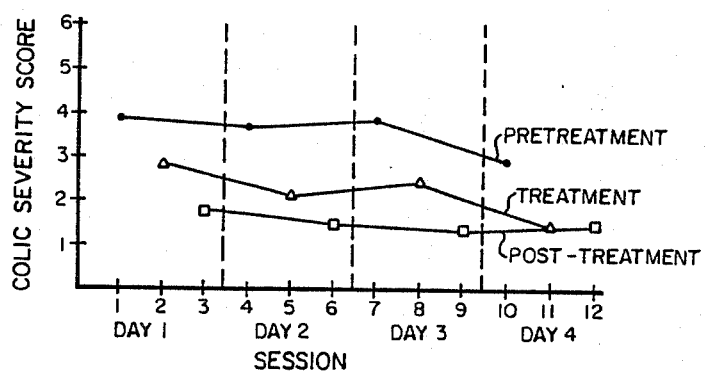
FIG. 5 is a graph showing the data gathered during the high motion rate and no sound of the invention.
Figure 6:
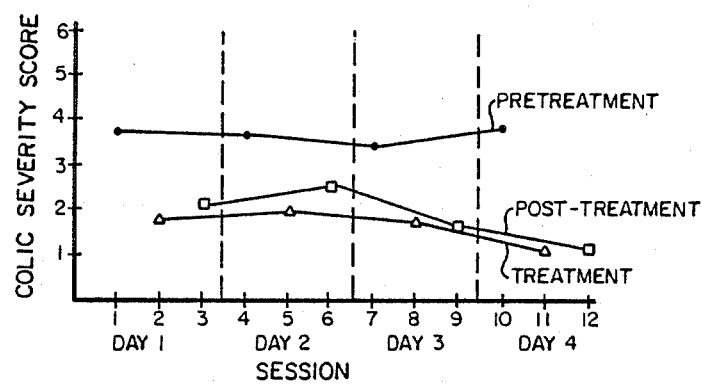
FIG. 6 is a graph showing the data gathered during the high motion rate and sound of the invention.

As seen in FIGS. 4, 5, and 6 surprisingly significant results are obtained for each of the groups where the invention is practiced within the range described above for experiment 1.

These results, coupled with tests of the first phase, demonstrate the significance of practice of the invention within the ranges conceived in the invention.

Figure 7:
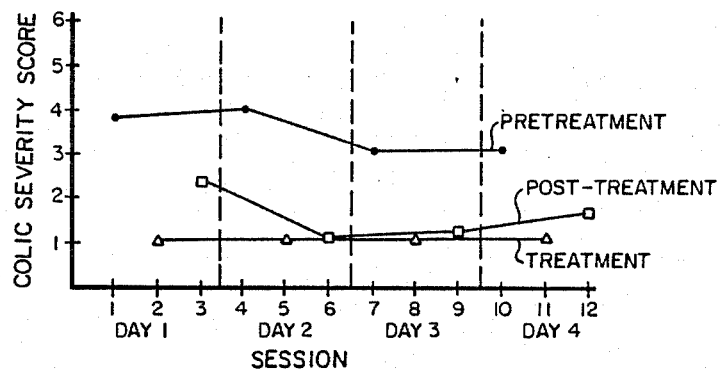
FIG. 7 is a graph showing a summary of the data obtained in all the treatments of experiment I.

Referring to FIG. 7, the dramatic improvement in colic severity level (score) is apparent by the large space between the pre-treatment curve and the treatment or post-treatment curves. It is of note, that the score remains low after the treatment for a considerable period of time, not returning to the higher pre-treatment level.

Figure 8:
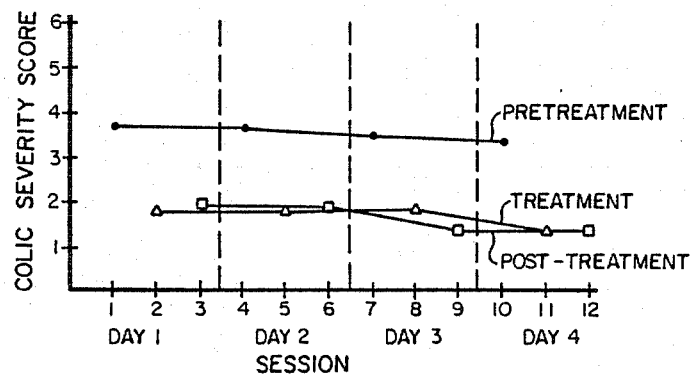
FIG. 8 is a summary of the data obtained from the low MS/sound group of subjects obtained in experiment I.

In FIG. 8, the distance between the pre-treatment curve and the treatment curve is even greater and shows uniform effectiveness on successive days.

Experimental I Research Data

| SUBJECTS TREATED | IMPROVED | COLIC SCORE SEVERITY EFFECTIVENESS LEVEL | PERCENTAGE OF SUBJECTS IMPROVED |
|---|---|---|---|
| 50 | 47 | 0.1 or more | 94% |
| 50 | 44 | 0.5 or more | 88% |
| 50 | 41 | 1.0 or more | 82% |
| 50 | 25 | 2.0 or more | 50% |

The above depicts that 82% of the subjects on an overall mean basis achieved a minimum of 1.0 colic score drop which is highly significant.

Below is the 50 subject breakdown by group:

|  | SUBJECTS PER GROUP | PRE-TREATMENT MEAN | TREATMENT MEAN | COLIC SCORE DROP MEAN |
|---|---|---|---|---|
| Low Vibration/ no sound | 12 | 3.3 | 1.5 | 1.8 |
| Low Vibration/ sound | 11 | 3.6 | 1.1 | 2.5 |
| High Vibration/ no sound | 13 | 3.4 | 2.2 | 1.2 |
| High Vibration/ sound | 14 | 3.5 | 1.7 | 1.8 |

The treatment of low vibration with sound is the most effective with a 2.5 mean point score drop. Not only does it demonstrate highly significant colic severity effectiveness results but practical implications by soothing the baby from an at least crying state to a non-crying relaxed mode.

Overall, sound treatment with MR has a positive effect on colic severity; however, most is attributed to the cell with low vibration and sound.

NUMBER OF INFANTS EXHIBITING IMPROVEMENT IN COLIC SCORES BETWEEN PRETREATMENT AND TREATMENT PERIODS BY TREATMENT CONDITION

| Improvement Range | Treatment Condition | | | |
|---|---|---|---|---|
| | Low Motion | | High Motion | |
| | No Sound | Sound | No Sound | Sound |
| 0–.49 | 1 | 0 | 4 | 2 |
| .5–.99 | 1 | 0 | 0 | 1 |
| 1.0–1.49 | 1 | 3 | 4 | 3 |
| 1.5–1.99 | 1 | 0 | 2 | 1 |
| 2.0–2.49 | 3 | 3 | 1 | 3 |
| 2.5–2.99 | 3 | 2 | 1 | 1 |
| 3.0–3.49 | 1 | 0 | 0 | 1 |
| 3.5–4.0 | 1 | 4 | 0 | 2 |
| TOTAL | 12 | 12 | 12 | 14 |

*It is important to note that the treatment condition (Low Motion Rate/Sound) exhibits as follows:
(1) 100% of the infants experienced a colic drop of at least 1 score.
(2) Over 75% of the infants experienced a colic drop of at least 2 scores.

The significance of having conceived and discovered a predictable range of operating characteristics of amplitude, frequency, and sound, and having obtained a beneficial therapeutic effect can not be minimized, since consideration should be given to the large amount of distress and discomfort that is alleviated when even a small and incrementally advantageous result can be obtained predictably by following the practice of the invention.

It has been found in the practice of this invention that each individual infant may have a different "resonance" of frequency, amplitude and sound of rhythmic cyclic motion mostly within the ranges established in the practice of the invention. Therefore is a further and more refined practice of the invention, parents or other persons taking care of the infant may find that adjustments to larger or smaller amplitude or to slower or faster frequency, and sound within the range, may have more beneficial effects. These adjustments are another step in the refined practice of the invention and this may be carried out by moving the position of the switch 55 by means of the knob 56. Although not as convenient, adjustments may be made in the "throw" of the eccentric weights 42 by adjusting their positions on the arms 48 by means of the screws 49.

Results of a further study have shown that the mother reported a high stress level prior to treatment. This was reflected in the reported stress level during the three days of baseline data. However, the reported stress level of the mother decreased substantially over the ten day treatment period as the low motion simulation and sound reduced the infants' colic behavior. There was direct concomitant variation between the infant colic behavior and the mothers' reported level of stress. Following the 10 days of treatment, the level of the mothers' reported stress continued to be monitored. With no treatment in place, there was a systematic rise in the stress level. See FIG. 9.

Although the power unit described herein is an electric motor, other power units might possibly be used, such as a hand-wound spring-driven "windup" power unit, or an electrical impulse solenoid/coil motor with associated timing devices to control the amplitude and frequency within the required range.

It is herein understood that although the present invention has been specifically disclosed with the preferred embodiment and example, modifications and variations of the concept herein disclosed may be resorted to by those skilled in the art.

For instance, it is conventional practice to support infants in reclining seat-like carriers, some of which are particularly adapted to fit on automobile or airplane seats. Others are useful in resting an infant in a comfortable position on a table, a bed, or on the floor. The apparatus and methods of this invention could be applied in the use of such carriers and surfaces.

I claim:

1. An apparatus for soothing and pacifying, specifically in infant suffering from colic, said apparatus adapted to be supported on a support means such as an infants crib, and comprising in combination:
   a. means for imparting a rhythmic cyclic motion of displacement to the support means and creating on the surface of the support means a frequency of displacement between about ten and about forty-three cycles per second, with the amplitude of the displacement between being about one hundredth and about one eighth of an inch; and
   b. means for, selectively and simultaneously with the means of step a, imparting a steady or unpulsed sound within the hearing range of the infant, and means for controlling the sound range within an intensity range of substantially between about sixty decibels and about eighty decibels within a frequency range of substantially between about two hundred Hertz and about four thousand Hertz.

2. An apparatus according to claim 1 wherein the motion imparting means comprises:
   a power unit operable to rotate an eccentrically positioned weight about an axis of rotation, with the axis substantially fixed relative to the support means of the infant.

3. An apparatus according to claim 2 wherein the power unit comprises an electric motor.

4. An apparatus according to claim 3 wherein the shaft of the motor comprises the axis of rotation for the eccentrically positioned weight.

5. An apparatus according to claim 1 wherein the means for imparting a cyclic motion comprises an electric coil or windup motor.

6. A method for soothing and pacifying, specifically an infant suffering from colic, said method being adapted to be practiced on a support means such as an infants cribe, and comprising:
   a. placing the infant on a supporting surface in a comfortable position; and
   b. imparting a rhythmic cyclic motion of displacement to the supporting surface and creating on the surface a rhythmic cyclic motion at a frequency between about ten cycles per second and about forty-three cycles per second, with the amplitude of displacement between about one hundredth of an inch and about one eighth of an inch.
   c. imparting, selectively and simultaneously with step b., a steady and unpulsed sound within the hearing range of the infant, and controlling the sound within an intensity range of between about sixty decibels and about eighty decibels within a frequency range of substantially between about two hundred Hertz and about four thousand Hertz.

7. The method of claim 6 including a further step of:
   d. adjusting the frequency within the range in step b. for maximum pacification of the infant.

8. The method of claim 6 including a further step:
   e. adjusting the amplitude of displacement within the range in step b. for maximum pacification the infant.

9. The method of claim 8 including a further step of adjusting the frequency within the range in step b. for maximum pacification of the infant.

* * * * *